United States Patent
Downer et al.

(10) Patent No.: US 8,377,076 B2
(45) Date of Patent: Feb. 19, 2013

(54) LENS DELIVERY SYSTEM

(75) Inventors: David Anthony Downer, Fort Worth, TX (US); Kyle Brown, Fort Worth, TX (US); Dengzhu Yan, Arlington, TX (US); Marshall Keith Proulx, Keller, TX (US); Sushant Muchhala, Kennedale, TX (US); Tu Cam Tran, Grapevine, TX (US)

(73) Assignee: Novartis AG, Basel (CH)

( * ) Notice: Subject to any disclaimer, the term of this patent is extended or adjusted under 35 U.S.C. 154(b) by 205 days.

(21) Appl. No.: 12/792,898

(22) Filed: Jun. 3, 2010

(65) Prior Publication Data
US 2010/0312254 A1    Dec. 9, 2010

Related U.S. Application Data

(60) Provisional application No. 61/185,428, filed on Jun. 9, 2009.

(51) Int. Cl.
*A61F 9/00*    (2006.01)
(52) U.S. Cl. ................. 606/107; 623/6.12
(58) Field of Classification Search ........... 606/107, 606/166; 623/6.11, 6.12
See application file for complete search history.

(56) References Cited

U.S. PATENT DOCUMENTS

| | | | |
|---|---|---|---|
| 4,681,102 | A | 7/1987 | Bartell |
| 5,275,604 | A | 1/1994 | Rheinish et al. |
| 5,494,484 | A | 2/1996 | Feingold |
| 5,499,987 | A | 3/1996 | Feingold |
| 5,616,148 | A | 4/1997 | Eagles et al. |
| 5,620,450 | A | 4/1997 | Eagles et al. |
| 5,653,715 | A | 8/1997 | Reich et al. |
| 6,537,283 | B2 * | 3/2003 | Van Noy ............ 606/107 |
| 7,156,854 | B2 | 1/2007 | Brown et al. |
| 2005/0149057 | A1 | 7/2005 | Rathert |

FOREIGN PATENT DOCUMENTS

EP    1958594    8/2008
WO    WO 2007/080868    7/2007

OTHER PUBLICATIONS

International Search Report for PCT/US2010/037374, 3 pages, 2010.
Written Opinion for PCT/US2010/037374, 7 pages, 2010.

* cited by examiner

*Primary Examiner* — Victor Nguyen
(74) *Attorney, Agent, or Firm* — Darien Reddick

(57) ABSTRACT

An intraocular lens delivery system includes an injector body having a bore surrounded by an inner wall. The system further includes a plunger configured to fit within the bore. The system also includes a plurality of deflectable members connected to the plunger and configured to contact the inner wall and to be deflected when the plunger is inserted within the bore. The deflectable members center the shaft and, when inserted within the injector body, contribute to producing a predetermined force resisting advancement of the plunger when deflected in the bore.

6 Claims, 2 Drawing Sheets

LENS DELIVERY SYSTEM

RELATED APPLICATIONS

This application claims priority to U.S. provisional application Ser. No. 61/185,428, filed on Jun. 9, 2009, the contents which are incorporated herein by reference.

FIELD OF THE INVENTION

This invention relates to intraocular lenses (IOLs) and more particularly to devices use to inject IOLs into an eye.

BACKGROUND OF THE INVENTION

The human eye in its simplest terms functions to provide vision by transmitting and refracting light through a clear outer portion called the cornea, and further focusing the image by way of the lens onto the retina at the back of the eye. The quality of the focused image depends on many factors including the size, shape and length of the eye, and the shape and transparency of the cornea and lens. When trauma, age or disease cause the lens to become less transparent, vision deteriorates because of the diminished light which can be transmitted to the retina. This deficiency in the lens of the eye is medically known as a cataract. The treatment for this condition is surgical removal of the lens and implantation of an artificial lens or IOL.

While early IOLs were made from hard plastic, such as polymethylmethacrylate (PMMA), soft, foldable IOLs made from silicone, soft acrylics and hydrogels have become increasingly popular because of the ability to fold or roll these soft lenses and insert them through a smaller incision. Several methods of rolling or folding the lenses are used. One popular method is an injector cartridge that folds the lenses and provides a relatively small diameter lumen through which the lens may be pushed into the eye, usually by a soft tip plunger, such as the one described in U.S. Pat. No. 4,681,102 (Bartell), which includes a split, longitudinally hinged cartridge. Similar designs are illustrated in U.S. Pat. Nos. 5,494,484 and 5,499,987 (Feingold) and 5,616,148 and 5,620,450 (Eagles, et al.). Other cartridge designs include, for example, U.S. Pat. Nos. 5,275,604 (Rheinish, et al.) and 5,653,715 (Reich, et al.).

It is desirable for any combination of cartridge and handpiece used in an intraocular lens delivery system to be comfortable and intuitive for the surgeon to use. An intraocular lens delivery system with a good "feel" for the surgeon can improve the ease and success rate of surgical procedures in which the intraocular lens delivery system is employed.

BRIEF SUMMARY OF THE INVENTION

In a particular embodiment of the present invention, an intraocular lens delivery system includes an injector body having a bore surrounded by an inner wall. The system further includes a plunger configured to fit within the bore. The system also includes a plurality of deflectable members connected to the plunger and configured to contact the inner wall and to be deflected when the plunger is inserted within the bore. The deflectable members center the shaft and, when inserted within the injector body, contribute to producing a predetermined force resisting advancement of the plunger when deflected in the bore.

In another embodiment of the present invention, a method of manufacturing an intraocular lens delivery system includes determining a resistance force to advancement of a plunger within an injector body having a bore surrounded by an inner wall. The method also includes determining a shape for a plurality of deflecting members connected to the plunger that will deflect when the plunger is received within the bore of the injector body to contribute to producing the predetermined resistance force. The method further includes manufacturing an intraocular lens delivery system including the injector body, the plunger, and the plurality of deflecting members.

Other objects, features and advantages of the present invention will become apparent with reference to the drawings, and the following description of the drawings and claims.

DETAILED DESCRIPTION OF THE INVENTION

Figure 1:
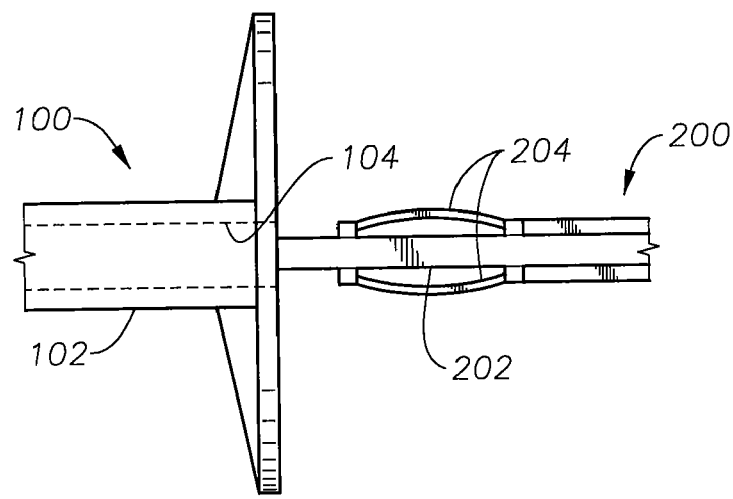
FIG. 1 illustrates an intraocular lens delivery system according to a particular embodiment of the present invention.

FIG. 1 illustrates an intraocular lens delivery system 100 according to a particular embodiment of the present invention. The delivery system 100 includes an injector body 102 having a bore 104 along with a plunger 200 to advance an intraocular lens within the injector body 102. As used within this specification, the term "injector body," an example of which is injector body 102, refers to any portion, components, or collection of components enclosing a bore 104 through which the plunger 200 advances when pushing the intraocular lens. The term "plunger" describes any component advanced through the bore 104 to push an intraocular lens through the injector body, which can be (but need not be) connected to other components of the intraocular lens delivery system 100. In particular, plungers 200 of various embodiments of the present invention may be made compatible with the lens delivery systems described in detail in U.S. Pat. No. 7,156,854 to Brown et al., which is incorporated herein by reference.

In particular embodiments, the entire injector body 102 may be formed as a single piece from a suitable material, which may include, for example, polypropylene or polyethylene. In other embodiments, the injector body 102 may be formed by coupling part of a reusable handpiece that forms a continuous bore 104 to a disposable cartridge holding the intraocular lens having a nozzle portion for injecting the intraocular lens through a surgical incision. Various embodiments may also include a lubricious coating within the bore 104 of the injector body 102 to facilitate advancement of the intraocular lens. However, one difficulty with previous intraocular lens delivery systems is that the plungers may also slide too easily within the bore 104, thus removing any real tactile feedback during advancement of the intraocular lens. Particular embodiments of the present invention provide a solution to this difficulty by producing a resistance to advancement of the plunger 200, as described in greater detail below.

Figure 2A:
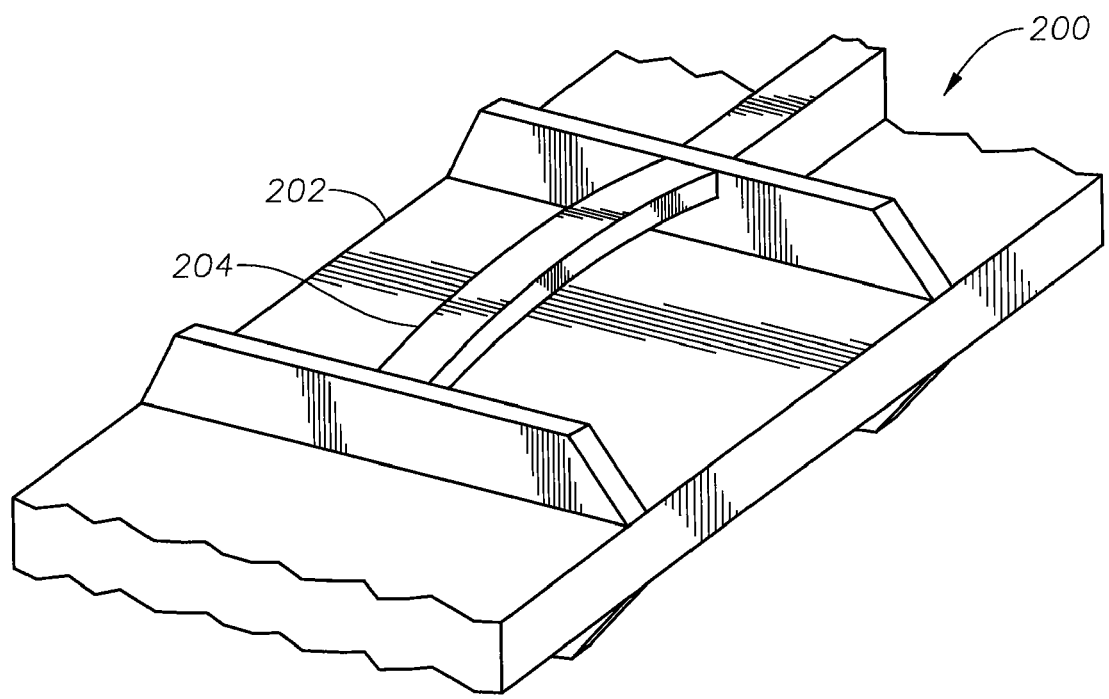
FIGS. 2A and 2B show different views of a plunger according to a particular embodiment of the present invention.
Figure 2B:
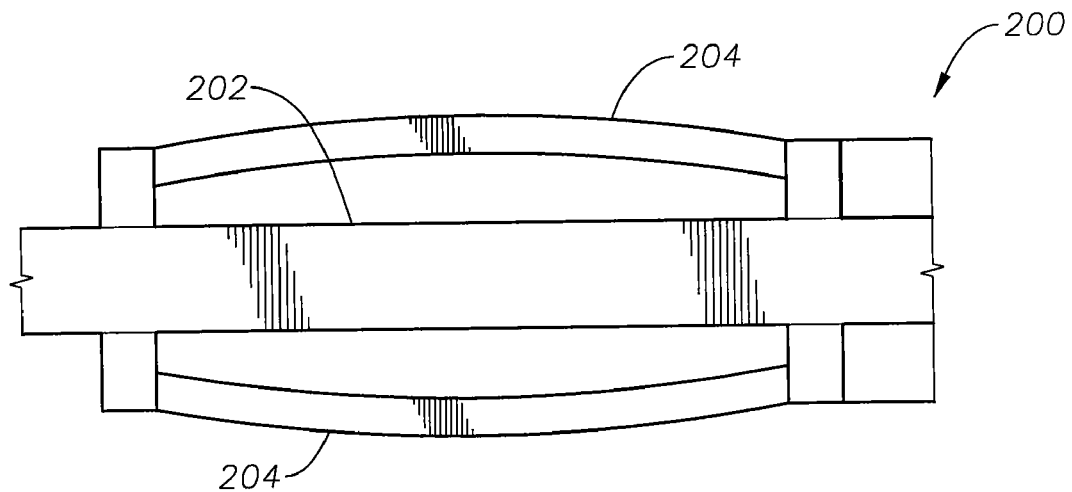

The plunger 200 pushes the intraocular lens by advancing a shaft 202 of the plunger 200 through the bore 104. Coupled to the plunger 200 are two deflectable members 204 on opposite sides of the plunger 200. FIGS. 2A and 2B show additional views of the deflectable members 204 of FIG. 1. In the depicted embodiment, the deflectable members 204 are arc-shaped, resilient extensions from the shaft 202 of the plunger 200. The peaks of the deflectable member 204 are configured to contact and to be deflected by an inner wall of the injector body 102 when the plunger 200 is placed within the bore 104.

The resulting force from the deflection of the deflectable members 204 helps to position the plunger 200 within the bore 104 so that the shaft 202 of the plunger 200 is reliably oriented relative to the intraocular lens. The deflectable members 204 also fit sufficiently tightly within the bore 104 that, when the deflectable members 204 are compressed by the inner wall of the injector body 102, the friction against the inner wall resists advancement of the plunger 200. This produces a tactile resistance to the plunger 200 sliding through the bore 104, which in turn both assists the surgeon in realizing when the plunger 200 is correctly engaged in the intraocular lens delivery system 100 and provides a steady resistance that facilitates controlled application of force during the lens delivery process.

Because the resistance varies with the force produced by deflection of the deflectable members 204, it is possible to adjust a design for the deflectable members 204 in order to vary the resistance of the intraocular lens delivery system 100.

Advantageously, the force can be adjusted to correspond to a desired "feel" for surgeons. For example, the resistance may be calibrated based on a survey of physicians to evaluate what resistance feels most suitable. In another example, typical resistance forces for handpieces of intraocular lens delivery systems preferred by various surgeons can be measures, and the deflectable members 204 can be adjusted to produce a suitable resistance. In yet another example, multiple different resistance values can be selected for multiple intraocular lens delivery systems 100, allowing physicians to choose plungers 200 that are relatively "stiff" (i.e., having high resistance to advancement) or plungers 200 that are relatively "yielding" (i.e., having lower resistance to advancement).

The deflectable members 204 can be formed separately from the plunger 200 or formed simultaneously as a single piece with the plunger 200 from a selected material suitable for use in ophthalmic applications, e.g., polypropylene. Forming the plunger 200 with the deflectable members 204 as a single piece has an advantage in reducing the number of manufacturing steps using techniques such as injection molding. The resistance force created by the deflectable members 204 can then be adjusted by varying the shape of the deflectable members 204 with respect to a selected material, so that plungers 200 with characteristic resistances can be produced. Alternatively, the same shape for the deflectable members 204 could be used with a variety of selected materials of different resiliency. In general, any adjustment known to be suitable to change the resistance of the plunger 200 to advancement may be employed.

Multiple deflectable members 204 placed along the plunger 200 could also be used to help the stability of the plunger 200. Thus, for example, one pair of deflectable members 204 could be placed closer to a distal end of the plunger 200 ("distal" in this context referring to an end of the plunger 200 configured to be placed nearest the incision during lens injection), while another pair is placed nearer to a proximal end ("proximal" referring to the end farthest from the incision during lens injection). Such configurations of deflectable members 204 can help to keep the plunger 200 aligned within the bore 104 as it is advanced.

Figure 3:
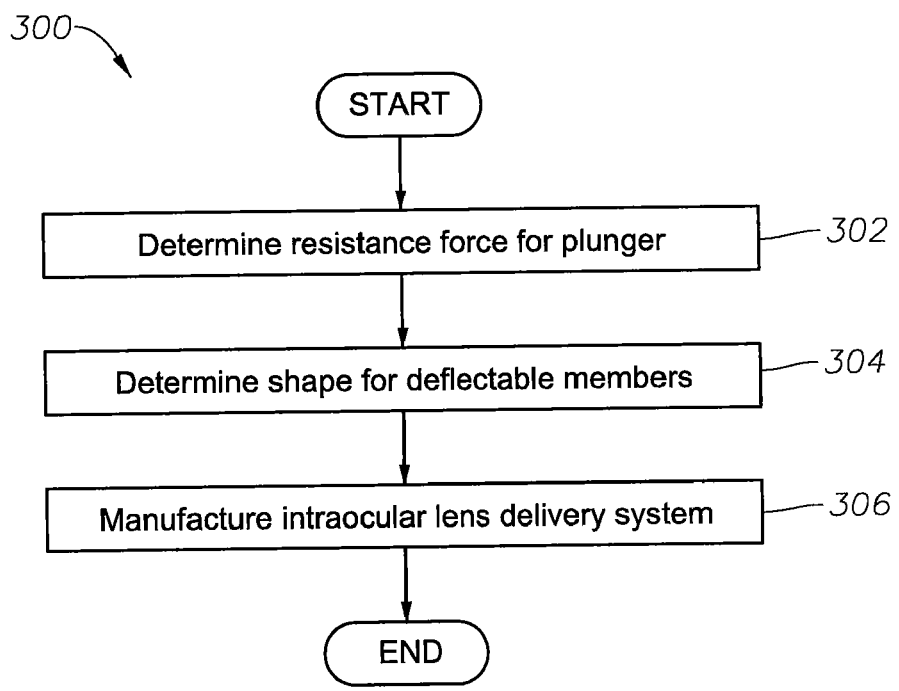
FIG. 3 is a flowchart showing an example method of manufacturing an intraocular lens delivery system according to another embodiment of the present invention.

FIG. 3 is a flowchart 300 illustrating an example method of manufacturing an intraocular lens delivery system 100 according to a particular embodiment of the present invention. At step 302, a desired resistance to advancement of a plunger 200 for the intraocular lens delivery system 100 is determined. The desired resistance may be determined based on a survey of physicians using various designs, force measurements of lens delivery systems used by the physicians, theoretical calculations based on the overall sources of resistance in the system 100, or a combinations of these techniques and/or any other suitable techniques for determining the value. At step 304, a shape for at least two deflectable members 204 is determined so that the deflectable members 204 hold the plunger 200 within the bore 104 and provide the predetermined resistance to advancement of the plunger 200. The deflectable members 204 may be designed according to any of the various considerations described above, including consideration of the material for the deflectable members 204 in determining the shape of the deflectable members 204. Steps 302 and 304 may also be repeatedly iteratively, such as particular designs being made and evaluated by physicians providing feedback used in the next design iteration. Finally, at step 306, the intraocular lens delivery system 100 is manufactured. Suitable manufacturing techniques may include injection molding, press formation, lathing, or any other technique known for forming the material in the art.

In a variation of the method presented above, multiple plungers 200 for intraocular lens delivery systems 200 with different resistances can be manufactured by selecting different forces at step 302. In particular embodiments of this variant method, step 302 may include selection of multiple resistance values based on considerations similar to the ones described above to provide for different surgical needs. Likewise, multiple designs for the deflectable members 204 may be determined that correspond to the different resistances, and step 306 would then include the manufacture of multiple plungers 200 along with injector bodies 102 that may be either common to the various plungers 200 or customized to work with plungers 200 having particular deflectable members 204. Although this particular variation has been described in detail, it should also be understood that other variations to the manufacturing method consistent with the description of the various embodiments of the intraocular lens delivery system 100 described herein could also be employed.

While certain embodiments of the present invention have been described above, these descriptions are given for purposes of illustration and explanation. Variations, changes, modifications and departures from the devices and methods disclosed above may be adopted without departure from the scope of the present invention as claimed.

What is claimed is:

1. An intraocular lens delivery system, comprising:
an injector body having a bore surrounded by an inner wall;
a plunger configured to fit within the bore; and
a plurality of deflectable members connected to the plunger and configured to contact the inner wall and to be deflected when the plunger is inserted within the bore, wherein the deflectable members center a shaft and wherein the plurality of deflectable members, when inserted within the injector body, contribute to producing a predetermined force resisting advancement of the plunger when deflected in the bore; wherein the plurality of deflectable members comprises a first pair of deflectable members and a second pair of deflectable members, wherein the first pair is closer to a distal end of the plunger than the second pair.

2. The system of claim 1, wherein the deflectable members are arc-shaped and configured such that a peak of each arc-shaped deflectable members contacts the inner wall.

3. The system of claim 1, wherein the predetermined force resisting advancement of the plunger is based on a survey of a plurality of physicians.

4. The system of claim 1, wherein the plunger and the plurality of deflectable members are formed as a single piece from a material.

5. The system of claim 4, wherein the material is selected from polypropylene or polyethylene.

6. The system of claim 1 wherein the plunger comprises:
the shaft; and
a plurality of protrusions extend from the shaft,
wherein the deflectable members are arc-shaped and configured such that a peak of each arc-shaped deflectable members contacts the inner wall, and
wherein each of the deflectable members extends between a pair of the plurality of protrusions.

* * * * *